(12) United States Patent
Li et al.

(10) Patent No.: US 7,951,933 B2
(45) Date of Patent: May 31, 2011

(54) CD38 SPLICE VARIANTS AND USES THEREOF

(75) Inventors: Jun Li, Danbury, CT (US); Xiang Li, Danbury, CT (US); Baerbel LoSacco, New Milford, CT (US); Zhenhao Qi, Sandy Hook, CT (US)

(73) Assignee: Boehringer Ingelheim Pharmaceutical, Inc., Ridgefield, CT (US)

( * ) Notice: Subject to any disclaimer, the term of this patent is extended or adjusted under 35 U.S.C. 154(b) by 621 days.

(21) Appl. No.: 11/056,106

(22) Filed: Feb. 10, 2005

(65) Prior Publication Data
US 2005/0202482 A1 Sep. 15, 2005

Related U.S. Application Data

(60) Provisional application No. 60/544,369, filed on Feb. 13, 2004.

(51) Int. Cl.
| | |
|---|---|
| C07H 21/02 | (2006.01) |
| C07H 21/04 | (2006.01) |
| C12Q 1/68 | (2006.01) |
| C12P 19/34 | (2006.01) |
| C12N 5/00 | (2006.01) |
| C12N 5/02 | (2006.01) |

(52) U.S. Cl. ............. 536/24.5; 536/23.1; 536/24.3; 536/24.33; 435/6; 435/91.1; 435/325; 435/375

(58) Field of Classification Search .................. None
See application file for complete search history.

(56) References Cited

U.S. PATENT DOCUMENTS

| | | | |
|---|---|---|---|
| 6,184,212 B1 * | 2/2001 | Miraglia et al. | 514/44 A |
| 6,607,879 B1 | 8/2003 | Cocks et al. | |
| 2002/0164788 A1 | 11/2002 | Ellis et al. | |

FOREIGN PATENT DOCUMENTS

| | | |
|---|---|---|
| WO | WO 94/17184 | 8/1994 |
| WO | WO 00/14116 | 3/2000 |

OTHER PUBLICATIONS

Jackson et al. The Journal of Immunology, vol. 144, No. 7, Apr. 1, 1990, pp. 2811-2815.*
GenBank Accession No. M34461, Jun. 19, 1995.*
Waterston, R.H., GenBank Accession No. AC092459, 2001, see IDS.*
GenBank Accession No. AC006425 downloaded from http://www.ncbi.nlm.nih.gov/ on Jun. 2, 2010.*
GenBank Accession No. AC005798 downloaded from http://www.ncbi.nlm.nih.gov/ on Jun. 2, 2010.*
Hammond et al. (Nature Reviews Genetics 2001, vol. 2:110-119).*
Koji Nata, et al. "Human gene encoding CD38 (ADP-ribosyl cyclase/cyclic ADP-ribose hydrolase): organization, nucleotide sequence and alternative splicing" Gene vol. 186, 1997, p. 285-292.

(Continued)

*Primary Examiner* — Sean McGarry
*Assistant Examiner* — Terra Cotta Gibbs
(74) *Attorney, Agent, or Firm* — Michael P. Morris; Edward S. Lazer

(57) ABSTRACT

The invention provides for a substantially purified polypeptide referred to herein as CD38JL that is a CD38 splice variant comprised of the polypeptide of SEQ ID NO: 1 or a fragment thereof. The invention also provides methods for treating preventing and diagnosing disorders associated with expression of CD38JL.

5 Claims, 10 Drawing Sheets

OTHER PUBLICATIONS

Frances E. Lund, et al. "CD38: a new paradigm in lymphocyte activation and signal transduction", Immunological Reviews 1998, vol. 161, p. 79-93.

European Search Report dated Feb. 12, 2008, 5 pages.

D5: Database EMBL [Online] 2001, Anonymous: "*Homo sapiens* chromosome 4 clone CTD-2185J18" retrieved from EBI Database accession No. AC092459.

\* cited by examiner

FIG. 2

```
                          1                                                    50
CD38_human          (1)   MANCEFSPVSGDKPCCRLSRRAQLCLGVSILVLILVVVLAVVVPRWRQTW
CD38JL_human        (1)   --------------------------------------------------
Consensus           (1)

51                                                   100
CD38_human         (51)   SGPGTTKRFPETVLARCVKYTEIHPEMRHVDCQSVWDAFKGAFISKHPCN
CD38JL_human        (1)   --------------------------------------------------
Consensus          (51)

101                                                  150
CD38_human        (101)   ITEEDYQPLMKLGTQTVPCNKILLWSRIKDLAHQFTQVQRDMFTLEDTLL
CD38JL_human        (1)   -------MKLGTQTVPCNKILLWSRINDLAHQFTQVQRDMFTLEDTLL
Consensus         (101)         MKLGTQTVPCNKILLWSRIKDLAHQFTQVQRDMFTLEDTLL 151                                                  200
CD38_human        (151)   GYLADDLTWCGEFNTSKINYQSCPDWRKDCSNNPVSVFWKTVSRRFAEAA
CD38JL_human       (42)   GYLADDLTWCGEFNTSEALGPVGLPPDVEGEQ-SDFCWRP----------
Consensus         (151)   GYLADDLTWCGEFNTS 201                                                  250
CD38_human        (201)   CDVVHVMLNGSRSKIFDKNSTFGSVEVHNLQPEKVQTLEAWVIHGGREDS
CD38JL_human       (82)   --------------------------------------------------
Consensus         (201)

251                                                  300
CD38_human        (251)   RDLCQDPTIKELESIISKRNIQFSCKNIYRPDKFLQCVKNPEDSSCTSEI
CD38JL_human       (82)   --------------------------------------------------
Consensus         (251)
```

FIG. 6-1

```
       <----------------------------------------------------------------
  1    GAATTCGCAC CAGAAGAGCC CAACTCTGTC TTGGCGTCAG TATCCTGGTC CTGATCCTCG
       CTTAAGCGTG GTCTTCTCGG GTTGAGACAG AACCGCAGTC ATAGGACCAG GACTAGGAGC
       ------------------exonI-----------------------------------------
 61    TCGTGGTGCT CGCGGTGGTC GTCCCGAGGT GGCGCCAGCA GTGGAGCGGT CCGGGCACCA
       AGCACCACGA GCGCCACCAG CAGGGCTCCA CCGCGGTCGT CACCTCGCCA GGCCCGTGGT
       ----------------------------------------------------------------
121    CCAAGCGCTT TCCCGAGACC GTCCTGGCGC GATGCGTCAA GTACACTGAA ATTCATCCTG
       GGTTCGCGAA AGGGCTCTGG CAGGACCGCG CTACGCAGTT CATGTGACTT TAAGTAGGAC
       ------><=======================================================
181    AGATGAGAAA CAGCTAAAAG AAGTGAGTTG GGCCAGGCAC TGTGGCTCAC ACCTGTAATC
       TCTACTCTTT GTCGATTTTC TTCACTCAAC CCGGTCCGTG ACACCGAGTG TGGACATTAG
       ================================================================
241    CCAGCACTTT GGGAGGCCCA GGCAGGTGGA TCACTTAAGG TCAGGAGTAC AAGACCTGCC
       GGTCGTGAAA CCCTCCGGGT CCGTCCACCT AGTGAATTCC AGTCCTCATG TTCTGGACGG
       ================================================================
301    TGGCCAACAT GCTGAAACTC CGTCTCTACT AAAAATACAA AATTAGCCGG GTGTTGTGGC
       ACCGGTTGTA CGACTTTGAG GCAGAGATGA TTTTTATGTT TTAATCGGCC CACAACACCG
       ================================================================
361    GCGTGCCTGT AATCCCAGCT ACTCTGGAGA CTGAGGTGGG AGAATCGCTT GAACCCAGGA
       CGCACGGACA TTAGGGTCGA TGAGACCTCT GACTCCACCC TCTTAGCGAA CTTGGGTCCT
       ================================================================
421    GGAGGAGGTA GCACTGAACC AAGATCCAGC CTGGCCAAGA GAGTAAGACT CCGTCTCAAA
       CCTCCTCCAT CGTGACTTGG TTCTAGGTCG GACCGGTTCT CTCATTCTGA GGCAGAGTTT
       ====exonII=============================><----------------exonIII-------
481    ACCAAACCAA ACCAAACCAA AAAAGAAAC ATGTAGACTG CCAAAGTGTA TGGGATGCTT
       TGGTTTGGTT TGGTTTGGTT TTTTTCTTTG TACATCTGAC GGTTTCACAT ACCCTACGAA
       ----------------------------------------------------------------
541    TCAAGGGTGC ATTTATTTCA AAACATCCTT GCAACATTAC TGAAGAAGAC TATCAGCCAC
       AGTTCCCACG TAAATAAAGT TTTGTAGGAA CGTTGTAATG ACTTCTTCTG ATAGTCGGTG
       -----------------------------------------><---------------------
            M   K   L   G   T   Q   T   V   P   C   N   K   I   L   L   W   S   R   I   K
601    TAATGAAGTT GGGAACTCAG ACCGTACCTT GCAACAAGAT TCTTCTTTGG AGCAGAATAA
       ATTACTTCAA CCCTTGAGTC TGGCATGGAA CGTTGTTCTA AGAAGAAACC TCGTCTTATT
       --------------------exonIV-------------------------------------
            D   L   A   H   Q   F   T   Q   V   Q   R   D   M   F   T   L   E   D   T   L
661    AAGATCTGGC CCATCAGTTC ACACAGGTCC AGCGGGACAT GTTCACCCTG GAGGACACGC
       TTCTAGACCG GGTAGTCAAG TGTGTCCAGG TCGCCCTGTA CAAGTGGGAC CTCCTGTGCG
       --------------------------------------------------------<=====
            L   G   Y   L   A   D   D   L   T   W   C   G   E   F   N   T   S   S   E   A
721    TGCTAGGCTA CCTTGCTGAT GACCTCACAT GGTGTGGTGA ATTCAACACT TCCAGTGAGG
       ACGATCCGAT GGAACGACTA CTGGAGTGTA CCACACCACT TAAGTTGTGA AGGTCACTCC
       =================================================================
            L   G   P   V   G   L   P   R   D   V   E   G   E   Q   S   D   F   C   W   R
781    CTCTGGGCCC TGTGGGATTG CCCAGGGATG TGGAGGGTGA ACAGAGTGAC TTCTGCTGGA
       GAGACCCGGG ACACCCTAAC GGGTCCCTAC ACCTCCCACT TGTCTCACTG AAGACGACCT
       =================================================================
            P
841    GGCCCTGAAT GATTAGTGTG GAGGACAGAG CCACAGGCAC CCATCCTGAT GCCATCTATA
       CCGGGACTTA CTAATCACAC CTCCTGTCTC GGTGTCCGTG GGTAGGACTA CGGTAGATAT
       =================================================================
901    CTTATATTAG TCCATTTGTG TTGCTATTAA GGAATACCTG AGGCTGCGTA ATTTATAAAG
       GAATATAATC AGGTAAACAC AACGATAATT CCTTATGGAC TCCGACGCAT TAAATATTTC
       =================================================================
961    AAAAGAGGTT TATTTGACTC ACAGTTACGC AGGCTGTACA AGAAGTAGGG TACCAGCATC
       TTTTCTCCAA ATAAACTGAG TGTCAATGCG TCCGACATGT TCTTCATCCC ATGGTCGTAG
       =================================================================
1021   CACTTCGGGT GAAGGCCTGA GGCTGTTTCC ACTCATGGAG AAGGGGAAGG GGAGCTGGCA
       GTGAAGCCCA CTTCCGGACT CCGACAAAGG TGAGTACCTC TTCCCCTTCC CCTCGACCGT
       =================================================================
1081   TTTACAGAGA TCACATGGTG AGGGAGGAAA GCAAGGAGAG GTCAGGGGAG GTGCCAGGCT
       AAATGTCTCT AGTGTACCAC TCCCTCCTTT CGTTCCTCTC CAGTCCCCTC CACGGTCCGA
       =====================================================================
```

FIG. 6-2

```
1141    GTTTGTAATG ACCAGCTGTC CTGGGAACTA GTAGAGTAAG AACTCATTAC TATAAGGACA
        CAAACATTAC TGGTCGACAG GACCCTTGAT CATCTCATTC TTGAGTAATG ATATTCCTGT
        ==========================================================
1201    GCACCATGCC ATTCGTGCAG GATCATCCCT ATGACCCAAA CACCTCCTAC TAGTCCCGAG
        CGTGGTACGG TAAGCACGTC CTAGTAGGGA TACTGGGTTT GTGGAGGATG ATCAGGGCTC
        ==========================================================
1261    CTCCAACACT GGGGGTCGAA TTTCAACATA AGGTTTGGAG AGTTAAATAT CCAAACTATA
        GAGGTTGTGA CCCCCAGCTT AAAGTTGTAT TCCAAACCTC TCAATTTATA GGTTTGATAT
        ==========================================================
1321    GCACTACCCT TAATGGCAAC TCAGGCTGAT ATAAAGTAGC ATTCCCTGTT TTCTTGAAAA
        CGTGATGGGA ATTACCGTTG AGTCCGACTA TATTTCATCG TAAGGGACAA AAGAACTTTT
        ==========================================================
1381    ATTGACTTCA GAGTTGGGGA TTGCCCATGC TCCCTAATTC CCTTCTTTTG AGTGCTCACA
        TAACTGAAGT CTCAACCCCT AACGGGTACG AGGGATTAAG GGAAGAAAAC TCACGAGTGT
        ==========================================================
1441    TAGCCTGCTT CCGAATTCTT GGTATTTTGC TCTCTGTAAG GTCATCATTC AGGTCCAAAG
        ATCGGACGAA GGCTTAAGAA CCATAAAACG AGAGACATTC CAGTAGTAAG TCCAGGTTTC
        ----------------------------------------------------------
        ==========================================================
1501    AAGTCTAGAA CAGGATGAGG TCTCAGTGGG ACCTAGACCA AGGTTCTTGC TCTTCAGAAT
        TTCAGATCTT GTCCTACTCC AGAGTCACCC TGGATCTGGT TCCAAGAACG AGAAGTCTTA
        ==========================================================
1561    CATCACAGTA GCCATGGACT GGACTCTTCC ATCTCAGGCA CTGGCTTTGC CATCATTTTT
        GTAGTGTCAT CGGTACCTGA CCTGAGAAGG TAGAGTCCGT GACCGAAACG GTAGTAAAAA
        ==========================================================
1621    CAGATGTAGC CTTACCCTGC CCAGAAAGAC TCAACACCTC ACCAGGGGAA GGGATTTCCT
        GTCTACATCG GAATGGGACG GGTCTTTCTG AGTTGTGGAG TGGTCCCCTT CCCTAAAGGA
        ==========================================================
1681    ACAACCAAAA CCCTACTGCA GTTTTCACTT CTTTTTTTTT TCTTTTTGTT TATATGGTGG
        TGTTGGTTTT GGGATGACGT CAAAAGTGAA GAAAAAAAAA AGAAAAACAA ATATACCACC
        ==========================================================
1741    ATATTTTTAC TTTATATAGT TTTATTCTTA TTTTTACTGT TTTTCATTGT TTGTTTTTAA
        TATAAAAATG AAATATATCA AAATAAGAAT AAAAATGACA AAAAGTAACA AACAAAAATT
        ==========================================================
1801    AAGCTTATCT TATTATAGCT TCTTTGTCCC AGGTTTGCAT TACTTTCAAT TACAAAAATA
        TTCGAATAGA ATAATATCGA AGAAACAGGG TCCAAACGTA ATGAAAGTTA ATGTTTTTAT
        ======================>
1861    AAGCATGATT ATTTGAAAAA AAAAAAAAAA AAAACTCGAC
        TTCGTACTAA TAAACTTTTT TTTTTTTTTT TTTTGAGCTG
```

1   MKLGTQTVPC NKILLWSRIK DLAHQFTQVQ RDMFTLEDTL LGYLADDLTW
51  CGEFNTSSEA LGPVGLPRDV EGEQSDFCWR P

FIG. 7

```
        <------------------------------------------------------------
  1     GAATTCGCAC CAGAAGAGCC CAACTCTGTC TTGGCGTCAG TATCCTGGTC CTGATCCTCG
        CTTAAGCGTG GTCTTCTCGG GTTGAGACAG AACCGCAGTC ATAGGACCAG GACTAGGAGC
        -----------------------exonI---------------------------------
 61     TCGTGGTGCT CGCGGTGGTC GTCCCGAGGT GGCGCCAGCA GTGGAGCGGT CCGGGCACCA
        AGCACCACGA GCGCCACCAG CAGGGCTCCA CCGCGGTCGT CACCTCGCCA GGCCCGTGGT
        -------------------------------------------------------------
121     CCAAGCGCTT TCCCGAGACC GTCCTGGCGC GATGCGTCAA GTACACTGAA ATTCATCCTG
        GGTTCGCGAA AGGGCTCTGG CAGGACCGCG CTACGCAGTT CATGTGACTT TAAGTAGGAC
        -------><===================================================
181     AGATGAGAAA CAGCTAAAAG AAGTGAGTTG GGCCAGGCAC TGTGGCTCAC ACCTGTAATC
        TCTACTCTTT GTCGATTTTC TTCACTCAAC CCGGTCCGTG ACACCGAGTG TGGACATTAG
        ============================================================
241     CCAGCACTTT GGGAGGCCCA GGCAGGTGGA TCACTTAAGG TCAGGAGTAC AAGACCTGCC
        GGTCGTGAAA CCCTCCGGGT CCGTCCACCT AGTGAATTCC AGTCCTCATG TTCTGGACGG
        ============================================================
301     TGGCCAACAT GCTGAAACTC CGTCTCTACT AAAAATACAA AATTAGCCGG GTGTTGTGGC
        ACCGGTTGTA CGACTTTGAG GCAGAGATGA TTTTTATGTT TTAATCGGCC CACAACACCG
        ============================================================
361     GCGTGCCTGT AATCCCAGCT ACTCTGGAGA CTGAGGTGGG AGAATCGCTT GAACCCAGGA
        CGCACGGACA TTAGGGTCGA TGAGACCTCT GACTCCACCC TCTTAGCGAA CTTGGGTCCT
        ============================================================
421     GGAGGAGGTA GCACTGAACC AAGATCCAGC CTGGCCAAGA GAGTAAGACT CCGTCTCAAA
        CCTCCTCCAT CGTGACTTGG TTCTAGGTCG GACCGGTTCT CTCATTCTGA GGCAGAGTTT
        ====exonII==========================><------------------exonIII--------
481     ACCAAACCAA ACCAAACCAA AAAAAGAAAC ATGTAGACTG CCAAAGTGTA TGGGATGCTT
        TGGTTTGGTT TGGTTTGGTT TTTTTCTTTG TACATCTGAC GGTTTCACAT ACCCTACGAA
        -------------------------------------------------------------
541     TCAAGGGTGC ATTTATTTCA AAACATCCTT GCAACATTAC TGAAGAAGAC TATCAGCCAC
        AGTTCCCACG TAAATAAAGT TTTGTAGGAA CGTTGTAATG ACTTCTTCTG ATAGTCGGTG
        ---------------------------------------------->< ------------
                   M   K   L   G   T   Q   T   V   P   C   N   K   I   L   L   W   S   R   I   K
601     TAATGAAGTT GGGAACTCAG ACCGTACCTT GCAACAAGAT TCTTCTTTGG AGCAGAATAA
        ATTACTTCAA CCCTTGAGTC TGGCATGGAA CGTTGTTCTA AGAAGAAACC TCGTCTTATT
        ------------------exonIV------------------------------------
           D   L   A   H   Q   F   T   Q   V   Q   R   D   M   F   T   L   E   D   T   L
661     AGATCTGGC CCATCAGTTC ACACAGGTCC AGCGGGACAT GTTCACCCTG GAGGACACGC
        TTCTAGACCG GGTAGTCAAG TGTGTCCAGG TCGCCCTGTA CAAGTGGGAC CTCCTGTGCG
        -----------------------------------------------------<=====
           L   G   Y   L   A   D   D   L   T   W   C   G   E   F   N   T   S   S   E   A
721     TGCTAGGCTA CCTTGCTGAT GACCTCACAT GGTGTGGTGA ATTCAACACT TCCAGTGAGG
        ACGATCCGAT GGAACGACTA CTGGAGTGTA CCACACCACT TAAGTTGTGA AGGTCACTCC
        ============================================================
           L   G   P   V   G   L   P   R   D   V   E   G   E   Q   S   D   F   C   W   R
781     CTCTGGGCCC TGTGGGATTG CCCAGGGATG TGGAGGGTGA ACAGAGTGAC TTCTGCTGGA
        GAGACCCGGG ACACCCTAAC GGGTCCCTAC ACCTCCCACT TGTCTCACTG AAGACGACCT
        ============================================================
           P
841     GGCCCTGAAT GATTAGTGTG GAGGACAGAG CCACAGGCAC CCATCCTGAT GCCATCTATA
        CCGGGACTTA CTAATCACAC CTCCTGTCTC GGTGTCCGTG GGTAGGACTA CGGTAGATAT
        ============================================================
901     CTTATATTAG TCCATTTGTG TTGCTATTAA GGAATACCTG AGGCTGCGTA ATTTATAAAG
        GAATATAATC AGGTAAACAC AACGATAATT CCTTATGGAC TCCGACGCAT TAAATATTTC
        ============================================================
961     AAAAGAGGTT TATTTGACTC ACAGTTACGC AGGCTGTACA AGAAGTAGGG TACCAGCATC
        TTTTCTCCAA ATAAACTGAG TGTCAATGCG TCCGACATGT TCTTCATCCC ATGGTCGTAG
        ============================================================
1021    CACTTCGGGT GAAGGCCTGA GGCTGTTTCC ACTCATGGAG AAGGGGAAGG GGAGCTGGCA
        GTGAAGCCCA CTTCCGGACT CCGACAAAGG TGAGTACCTC TTCCCCTTCC CCTCGACCGT
        ============================================================
1081    TTTACAGAGA TCACATGGTG AGGGAGGAAA GCAAGGAGAG GTCAGGGGAG GTGCCAGGCT
        AAATGTCTCT AGTGTACCAC TCCCTCCTTT CGTTCCTCTC CAGTCCCCTC CACGGTCCGA
        ============================================================
```

Fig. 8-1

```
1141    GTTTGTAATG ACCAGCTGTC CTGGGAACTA GTAGAGTAAG AACTCATTAC TATAAGGACA
        CAAACATTAC TGGTCGACAG GACCCTTGAT CATCTCATTC TTGAGTAATG ATATTCCTGT
        ========== ========== ========== ========== ========== ==========
1201    GCACCATGCC ATTCGTGCAG GATCATCCCT ATGACCCAAA CACCTCCTAC TAGTCCCGAG
        CGTGGTACGG TAAGCACGTC CTAGTAGGGA TACTGGGTTT GTGGAGGATG ATCAGGGCTC
        ========== ========== ========== ========== ========== ==========
1261    CTCCAACACT GGGGGTCGAA TTTCAACATA AGGTTTGGAG AGTTAAATAT CCAAACTATA
        GAGGTTGTGA CCCCCAGCTT AAAGTTGTAT TCCAAACCTC TCAATTTATA GGTTTGATAT
        ========== ========== ========== ========== ========== ==========
1321    GCACTACCCT TAATGGCAAC TCAGGCTGAT ATAAAGTAGC ATTCCCTGTT TTCTTGAAAA
        CGTGATGGGA ATTACCGTTG AGTCCGACTA TATTTCATCG TAAGGGACAA AAGAACTTTT
        ========== ========== ========== ========== ========== ==========
1381    ATTGACTTCA GAGTTGGGGA TTGCCCATGC TCCCTAATTC CCTTCTTTTG AGTGCTCACA
        TAACTGAAGT CTCAACCCCT AACGGGTACG AGGGATTAAG GGAAGAAAAC TCACGAGTGT
        ========== ========== ========== ========== ========== ==========
1441    TAGCCTGCTT CCGAATTCTT GGTATTTTGC TCTCTGTAAG GTCATCATTC AGGTCCAAAG
        ATCGGACGAA GGCTTAAGAA CCATAAAACG AGAGACATTC CAGTAGTAAG TCCAGGTTTC
        ---------- ---------- ---------- ---------- ---------- ----------
        ========== ========== ========== ========== ========== ==========
1501    AAGTCTAGAA CAGGATGAGG TCTCAGTGGG ACCTAGACCA AGGTTCTTGC TCTTCAGAAT
        TTCAGATCTT GTCCTACTCC AGAGTCACCC TGGATCTGGT TCCAAGAACG AGAAGTCTTA
        ========== ========== ========== ========== ========== ==========
1561    CATCACAGTA GCCATGGACT GGACTCTTCC ATCTCAGGCA CTGGCTTTGC CATCATTTTT
        GTAGTGTCAT CGGTACCTGA CCTGAGAAGG TAGAGTCCGT GACCGAAACG GTAGTAAAAA
        ========== ========== ========== ========== ========== ==========
1621    CAGATGTAGC CTTACCCTGC CCAGAAAGAC TCAACACCTC ACCAGGGGAA GGGATTTCCT
        GTCTACATCG GAATGGGACG GGTCTTTCTG AGTTGTGGAG TGGTCCCCTT CCCTAAAGGA
        ========== ========== ========== ========== ========== ==========
1681    ACAACCAAAA CCCTACTGCA GTTTTCACTT CTTTTTTTTT TCTTTTTGTT TATATGGTGG
        TGTTGGTTTT GGGATGACGT CAAAAGTGAA GAAAAAAAAA AGAAAAACAA ATATACCACC
        ========== ========== ========== ========== ========== ==========
1741    ATATTTTTAC TTTATATAGT TTTATTCTTA TTTTTACTGT TTTTCATTGT TTGTTTTTAA
        TATAAAAATG AAATATATCA AAATAAGAAT AAAAATGACA AAAAGTAACA AACAAAAATT
        ========== ========== ========== ========== ========== ==========
1801    AAGCTTATCT TATTATAGCT TCTTTGTCCC AGGTTTGCAT TACTTTCAAT TACAAAAATA
        TTCGAATAGA ATAATATCGA AGAAACAGGG TCCAAACGTA ATGAAAGTTA ATGTTTTTAT
        ==========>==========> ==========> ==========> ==========> ==========>
1861    AAGCATGATT ATTTGAAAAA AAAAAAAAAA AAAACTCGAC
        TTCGTACTAA TAAACTTTTT TTTTTTTTT TTTTGAGCTG
```

FIG. 8-2

The longest Open reading frame of CD38JL (starting with 1ˢᵗ MET) is translated in the sequence panel of CD38 splice variant cDNA above (exon positions including boundary are labeled, sequences different from CD38 are under "=" sign).

SEQUENCE LISTING

```
<160> NUMBER OF SEQ ID NOS: 9

<210> SEQ ID NO 1
<211> LENGTH: 81
<212> TYPE: PRT
<213> ORGANISM: Homo sapiens

<400> SEQUENCE: 1

Met Lys Leu Gly Thr Gln Thr Val Pro Cys Asn Lys Ile Leu Leu Trp
 1               5                  10                  15

Ser Arg Ile Lys Asp Leu Ala His Gln Phe Thr Gln Val Gln Arg Asp
            20                  25                  30

Met Phe Thr Leu Glu Asp Thr Leu Leu Gly Tyr Leu Ala Asp Asp Leu
        35                  40                  45

Thr Trp Cys Gly Glu Phe Asn Thr Ser Ser Glu Ala Leu Gly Pro Val
    50                  55                  60

Gly Leu Pro Arg Asp Val Glu Gly Glu Gln Ser Asp Phe Cys Trp Arg
65                  70                  75                  80

Pro

<210> SEQ ID NO 2
<211> LENGTH: 1900
<212> TYPE: DNA
<213> ORGANISM: Homo sapiens
<220> FEATURE:
```

```
<221> NAME/KEY: CDS
<222> LOCATION: (603)..(845)

<400> SEQUENCE: 2
gaattcgcac cagaagagcc caactctgtc ttggcgtcag tatcctggtc ctgatcctcg      60
tcgtggtgct cgcggtggtc gtcccgaggt ggcgccagca gtggagcggt ccgggcacca     120
ccaagcgctt tcccgagacc gtcctggcgc gatgcgtcaa gtacactgaa attcatcctg     180
agatgagaaa cagctaaaag aagtgagttg ggccaggcac tgtggctcac acctgtaatc     240
ccagcacttt gggaggccca ggcaggtgga tcacttaagg tcaggagtac aagacctgcc     300
tggccaacat gctgaaactc cgtctctact aaaaatacaa aattagccgg gtgttgtggc     360
gcgtgcctgt aatcccagct actctggaga ctgaggtggg agaatcgctt gaacccagga     420
ggaggaggta gcactgaacc aagatccagc ctggccaaga gagtaagact ccgtctcaaa     480
accaaaccaa accaaaccaa aaaagaaac atgtagactg ccaaagtgta tgggatgctt      540
tcaagggtgc atttatttca aaacatcctt gcaacattac tgaagaagac tatcagccac     600 ta atg aag ttg gga act cag acc gta cct tgc aac aag att ctt ctt       647
   Met Lys Leu Gly Thr Gln Thr Val Pro Cys Asn Lys Ile Leu Leu
   1               5                  10                  15 tgg agc aga ata aaa gat ctg gcc cat cag ttc aca cag gtc cag cgg      695
Trp Ser Arg Ile Lys Asp Leu Ala His Gln Phe Thr Gln Val Gln Arg
            20                  25                  30 gac atg ttc acc ctg gag gac acg ctg cta ggc tac ctt gct gat gac      743
Asp Met Phe Thr Leu Glu Asp Thr Leu Leu Gly Tyr Leu Ala Asp Asp
        35                  40                  45 ctc aca tgg tgt ggt gaa ttc aac act tcc agt gag gct ctg ggc cct      791
Leu Thr Trp Cys Gly Glu Phe Asn Thr Ser Ser Glu Ala Leu Gly Pro
    50                  55                  60 gtg gga ttg ccc agg gat gtg gag ggt gaa cag agt gac ttc tgc tgg      839
Val Gly Leu Pro Arg Asp Val Glu Gly Glu Gln Ser Asp Phe Cys Trp
65                  70                  75 agg ccc tgaatgatta gtgtggagga cagagccaca ggcacccatc ctgatgccat       895
Arg Pro
 80 ctatacttat attagtccat ttgtgttgct attaaggaat acctgaggct gcgtaattta    955 taaagaaaag aggtttattt gactcacagt tacgcaggct gtacaagaag tagggtacca   1015 gcatccactt cgggtgaagg cctgaggctg tttccactca tggagaaggg gaaggggagc   1075 tggcatttac agagatcaca tggtgaggga ggaaagcaag gagaggtcag gggaggtgcc   1135 aggctgtttg taatgaccag ctgtcctggg aactagtaga gtaagaactc attactataa   1195 ggacagcacc atgccattcg tgcaggatca tccctatgac ccaaacacct cctactagtc   1255 ccgagctcca acactggggg tcgaatttca acataaggtt tggagagtta aatatccaaa   1315 ctatagcact acccttaatg gcaactcagg ctgatataaa gtagcattcc ctgtttctt    1375 gaaaaattga cttcagagtt ggggattgcc catgctccct aattcccttc ttttgagtgc   1435 tcacatagcc tgcttccgaa ttcttggtat tttgctctct gtaaggtcat cattcaggtc   1495 caaagaagtc tagaacagga tgaggtctca gtgggaccta gaccaaggtt cttgctcttc   1555 agaatcatca cagtagccat ggactggact cttccatctc aggcactggc tttgccatca   1615 tttttcagat gtagccttac cctgcccaga aagactcaac acctcaccag gggaagggat   1675 ttcctacaac caaaacccta ctgcagtttt cacttctttt ttttttcttt tgtttatat    1735 ggtggatatt tttactttat atagtttat tcttattttt actgtttttc attgtttgtt    1795 tttaaaagct tatcttatta tagcttcttt gtcccaggtt tgcattactt tcaattacaa   1855
```
aaataaagca tgattatttg aaaaaaaaaa aaaaaaaaac tcgac      1900

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaggtgttga gtctttctgg gca      23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atagcctgct tccgaattct tgg      23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccatgctcc ctaattccct tc      22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacagagctc gtttagtgaa cc      22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tagaaggaca cctagtcaga c      21

<210> SEQ ID NO 8
<211> LENGTH: 300
<212> TYPE: PRT
<213> ORGANISM: Homo sapiens

<400> SEQUENCE: 8

Met Ala Asn Cys Glu Phe Ser Pro Val Ser Gly Asp Lys Pro Cys Cys
 1               5                  10                  15

Arg Leu Ser Arg Arg Ala Gln Leu Cys Leu Gly Val Ser Ile Leu Val

```
                    20                  25                  30
Leu Ile Leu Val Val Leu Ala Val Val Pro Arg Trp Arg Gln
            35                  40                  45

Thr Trp Ser Gly Pro Gly Thr Thr Lys Arg Phe Pro Glu Thr Val Leu
        50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300

<210> SEQ ID NO 9
<211> LENGTH: 460
<212> TYPE: DNA
<213> ORGANISM: Homo sapiens

<400> SEQUENCE: 9
caaataatca tgctttattt ttgtaattga agtaatgca aacctgggac aaagaagcta      60
taataagata agcttttaaa aacaaacaat gaaaacagt aaaaataaga ataaaactat    120
ataaagtaaa aatatccacc atataaacaa aaagaaaaaa aaagaagtg aaaactgcag    180 tagggttttg gttgtaggaa atcccttccc ctggtgaggt gttgagtctt tctgggcagg    240
ataaggctac atctgaaaaa tgatggcaaa gccagtgcct gagatggaag agtccagtcc    300
atggctactg tgatgattct gaagagcaag aaccttggtc taggtcccac tgagacctca    360
tcctgttcta gacttctttg gacctgaatg atgaccttac agagagcaaa ataccaagaa    420
ttcggaagca ggctatgtga gcactcaaaa gaagggaatt                          460
```

CD38 SPLICE VARIANTS AND USES THEREOF

RELATED APPLICATIONS

This application claims benefit to U.S. provisional application No. 60/544,369 filed Feb. 13, 2004 and the contents are incorporated herein.

BACKGROUND OF THE INVENTION

1. Technical Field

The present invention relates generally to the fields of molecular biology and inflammation. More specifically, the present invention relates to the identification of novel variants of CD38 and uses thereof.

2. Background Information

T-lymphocytes bearing the CD4 receptor (CD4+), called CD4$^+$ T cells, augment the immune response by secreting cytokines that stimulate either a cytotoxic T cell response (T-helper 1) or an antibody response (T-helper 2). Naïve CD4$^+$ T cells can differentiate to Th1 or Th2 cells after the engagement of TCR-peptide-MHC class II complex, depending on the existing cytokines in the environment. Thus, CD4$^+$ T cells play critical roles in T cell-mediated immune responses. Novel genes that function in T cell activation may provide novel drug targets for autoimmune and inflammatory disease. Accordingly, the identification and characterization of novel genes which are involved in the activation of CD4$^+$ T cells is considered important.

CD38 is a multifunctional cell surface antigen that functions in cell adhesion, signal transduction and calcium signaling. CD38 catalyzes the production of cyclic ADP-ribose (cADPR) from its substrate NAD+. Takasawa, S. Et al. (1993) *J. Biol. Chem.* 268: 26052-26054. cADPR acts as a second messenger that regulates intracellular calcium release. CD38 is expressed in hematopoeitic cells including T lymphocytes, B lymphocytes and neutrophils. CD38−/− mice shows a complete loss of tissue-associated NAD+ glycohydrolase activity and exhibited marked deficiencies in antibody responses to T cell-dependent protein antigens. Cockayne, et al. (1998) *Blood* 92: 1324-1333. CD38 controls neutrophil chemotaxis to bacterial chemoattractants through its production of cyclic ADP-ribose, and acts as a critical regulator of inflammation and innate immune responses. Partida-Sanchez S, et al. (2002) *Nat Med* 7:1209-16. The human cDNA of CD38 was first cloned in 1990 and it encodes 300 amino acids. Jackson, D. G.; Bell, J. I. (1990) *J. Immun.* 144: 2811-2815. It was reported that the CD38 gene is present in a single copy and extends over more than 62 kb. It consists of 8 exons and 7 introns, including a long intron that interrupts the 5-prime coding region. Ferrero, E.; Malavasi, F. (1997) *J. Immun.* 159: 3858-3865. The structure of the CD38 protein is unknown.

Cell surface antigens like CD38 have been known to occur in different isoforms that are structurally and functionally different from one another. For example CXCR-3 has two isoforms, CXCR3A and CXCR3-B, that have been found to have different biological activities and to trigger different signal transduction pathways. CXCR3-B shows high affinity only for CXCL4 where CXR3-A does not. Lasagni L et al, J Exp Med. 2003, 197:1537-49).

One cDNA splicing isoform of CD38, which only encodes 122 amino acid residues, was isolated from a human testis library. (Nata, K. et al, 1997, *Gene* 186, 285292).

The discovery of a new isoform for CD38 and the polynucleotides encoding it satisfies a need in the art by providing new compositions which may be used in the treatment, prevention and diagnosis of autoimmune and immunological diseases.

BRIEF SUMMARY OF THE INVENTION

The invention provides for a substantially purified polypeptide referred to herein as CD38JL that is a CD38 splice variant comprised of 81 amino acid polypeptide of SEQ ID NO: 1 or a fragment thereof. Amino Acid residues 1 through 57 of SEQ. ID. NO. 1 correspond to amino acid residues found in the CD38 sequence and with which ADP-ribosylcyclase activity is associated.

SEQ ID NO: 2 shows the sequence of the cDNA clone LJ-2 that encodes CD38JL.

```
cDNA sequence for clone LJ-2 (SEQ ID NO: 2)
  1   GAATTCGCAC CAGAAGAGCC CAACTCTGTC TTGGCGTCAG TATCCTGGTC
 51   CTGATCCTCG TCGTGGTGCT CGCGGTGGTC GTCCCGAGGT GGCGCCAGCA
101   GTGGAGCGGT CCGGGCACCA CCAAGCGCTT TCCCGAGACC GTCCTGGCGC
151   GATGCGTCAA GTACACTGAA ATTCATCCTG AGATGAGAAA CAGCTAAAAG
201   AAGTGAGTTG GGCCAGGCAC TGTGGCTCAC ACCTGTAATC CCAGCACTTT
251   GGGAGGCCCA GGCAGGTGGA TCACTTAAGG TCAGGAGTAC AAGACCTGCC
301   TGGCCAACAT GCTGAAACTC CGTCTCTACT AAAAATACAA AATTAGCCGG
351   GTGTTGTGGC GCGTGCCTGT AATCCCAGCT ACTCTGGAGA CTGAGGTGGG
401   AGAATCGCTT GAACCCAGGA GGAGGAGGTA GCACTGAACC AAGATCCAGC
451   CTGGCCAAGA GAGTAAGACT CCGTCTCAAA ACCAAACCAA ACCAAACCAA
501   AAAAAGAAAC ATGTAGACTG CCAAAGTGTA TGGGATGCTT TCAAGGGTGC
551   ATTTATTTCA AAACATCCTT GCAACATTAC TGAAGAAGAC TATCAGCCAC
601   TAATGAAGTT GGGAACTCAG ACCGTACCTT GCAACAAGAT TCTTCTTTGG
651   AGCAGAATAA AAGATCTGGC CCATCAGTTC ACACAGGTCC AGCGGGACAT
701   GTTCACCCTG GAGGACACGC TGCTAGGCTA CCTTGCTGAT GACCTCACAT
```

-continued

```
 751  GGTGTGGTGA ATTCAACACT TCCAGTGAGG CTCTGGGCCC TGTGGGATTG
 801  CCCAGGGATG TGGAGGGTGA ACAGAGTGAC TTCTGCTGGA GGCCCTGAAT
 851  GATTAGTGTG GAGGACAGAG CCACAGGCAC CCATCCTGAT GCCATCTATA
 901  CTTATATTAG TCCATTTGTG TTGCTATTAA GGAATACCTG AGGCTGCGTA
 951  ATTTATAAAG AAAAGAGGTT TATTTGACTC ACAGTTACGC AGGCTGTACA
1001  AGAAGTAGGG TACCAGCATC CACTTCGGGT GAAGGCCTGA GGCTGTTTCC
1051  ACTCATGGAG AAGGGGAAGG GGAGCTGGCA TTTACAGAGA TCACATGGTG
1101  AGGGAGGAAA GCAAGGAGAG GTCAGGGGAG GTGCCAGGCT GTTTGTAATG
1151  ACCAGCTGTC CTGGGAACTA GTAGAGTAAG AACTCATTAC TATAAGGACA
1201  GCACCATGCC ATTCGTGCAG GATCATCCCT ATGACCCAAA CACCTCCTAC
1251  TAGTCCCGAG CTCCAACACT GGGGGTCGAA TTTCAACATA AGGTTTGGAG
1301  AGTTAAATAT CCAAACTATA GCACTACCCT TAATGGCAAC TCAGGCTGAT
1351  ATAAAGTAGC ATTCCCTGTT TTCTTGAAAA ATTGACTTCA GAGTTGGGGA
1401  TTGCCCATGC TCCCTAATTC CCTTCTTTTG AGTGCTCACA TAGCCTGCTT
1451  CCGAATTCTT GGTATTTTGC TCTCTGTAAG GTCATCATTC AGGTCCAAAG
1501  AAGTCTAGAA CAGGATGAGG TCTCAGTGGG ACCTAGACCA AGGTTCTTGC
1551  TCTTCAGAAT CATCACAGTA GCCATGGACT GGACTCTTCC ATCTCAGGCA
1601  CTGGCTTTGC CATCATTTTT CAGATGTAGC CTTACCCTGC CCAGAAAGAC
1651  TCAACACCTC ACCAGGGGAA GGGATTTCCT ACAACCAAAA CCCTACTGCA
1701  GTTTTCACTT CTTTTTTTTT TCTTTTTGTT TATATGGTGG ATATTTTTAC
1751  TTTATATAGT TTTATTCTTA TTTTTACTGT TTTTCATTGT TTGTTTTTAA
1801  AAGCTTATCT TATTATAGCT TCTTTGTCCC AGGTTTGCAT TACTTTCAAT
1851  TACAAAAATA AAGCATGATT ATTTGAAAAA AAAAAAAAAA AAAACTCGAC
```

The predicted longest open reading frame of this cDNA clone LJ-2 (starting from MET) is shown in SEQ ID NO: 1.

```
 1  MKLGTQTVPC NKILLWSRIK DLAHQFTQVQ RDMFTLEDTL LGYLADDLTW    SEQ ID NO: 1
51  CGEFNTSSEA LGPVGLPRDV EGEQSDFCWR P
```

The invention also provides for a substantially purified polypeptide fragment of CD38JL comprised of residues residues 58-81 of the polypeptide sequence of SEQ ID NO: 1.

The invention also provides an isolated and purified polynucleotide encoding the polypeptide comprised of the amino acid sequence of SEQ ID NO: 1 or a fragment of SEQ ID NO: 1 and in particular a fragment comprised of amino acid residues 58-81 of SEQ ID NO. 1.

The invention also provides for isolated and purified polynucleotides of 10 or more bases selected from SEQ ID NO: 2 and particularly bases 188-508 and 775-1884 of SEQ ID NO: 2.

The invention also provides an isolated and purified polynucleotide variant having at least 90% polynucleotide identity to the polynucleotide encoding the polypeptide consisting of the amino acid sequence of SEQ ID NO: 1 or a fragment thereof.

The invention further provides an isolated and purified polynucleotide which hybridizes under stringent conditions to the polynucleotide encoding the polypeptide consisting of the amino acid sequence of SEQ ID NO: 1 or a fragment of SEQ ID NO: 1, as well as an isolated and purified polynucleotide which is substantially complementary to the polynucleotide encoding the polypeptide consisting of the amino acid sequence of SEQ ID NO: 1 or a fragment of SEQ ID NO: 1.

The invention also provides for an expression vector containing at least a fragment of the polynucleotide encoding the polypeptide consisting of the amino acid sequence of SEQ ID NO: 1. In another embodiment the expression vector is contained in a host cell.

Another embodiment of the invention provides for a method of treating IBD (Inflamed Bowel Disease) comprising the step of administering to a patient in need thereof a therapeutically effective of CD38JL splice variant polypeptide inhibitor or antagonist.

Another embodiment of the invention provides for a method of treating IBD (Inflamed Bowel Disease) comprising the step of administering to a patient in need thereof a therapeutically effective of CD38JL splice variant agonist.

The present invention also provides a pharmaceutical composition comprising a substantially purified polypeptide of SEQ ID NO: 1 in conjunction with a suitable pharmaceutical carrier.

The invention also provides a method for treating or preventing IBD, Psoriasis, rheumatoid arthritis or autoimmune diseases, said method comprised of the steps of administering to a patient in need thereof an therapeutically effective amount a CD38JL inhibitor and or an antagonist.

Another embodiment of the invention relates to a method of treating inflammatory disease in a human comprising the step of administrating to a patient in need of such treatment a therapeutically acceptable amount of a CD38JL inhibitor. Such a method of treatment is likely to be useful in the treatment of IBD, Psoriasis, rheumatoid arthritis and autoimmune diseases.

The invention also provides a method for detecting a polynucleotide sequence encoding CD38JL in a biological sample containing nucleic acids, said method comprised of the steps of:

a) hybridizing the complement of the polynucleotide encoding the polypeptide comprising the sequence of SEQ ID NO: 1 or a fragment of SEQ ID NO: 1 to at least one of the nucleic acids of the biological sample, thereby forming a hybridization complex; and b) detecting the hybridization complex, wherein the presence of the hybridization complex correlates with the presence of a polynucleotide encoding CD38JL in the biological sample.

Another embodiment of the invention provides a purified antibody that binds specifically to a polypeptide of SEQ ID. NO. 1 or that binds specifically to polypeptides 58-81 of SEQ ID. NO. 1.

Other aspects, features and advantages of the present invention will be apparent from the following description of the presently preferred embodiments of the invention.

BRIEF DESCRIPTION OF THE FIGURES

FIG. 2 shows an alignment of the polypeptide sequence of CD38JL (SEQ ID NO: 1) and CD38 (SEQ ID NO: 8).

FIG. 6 shows the alignment of the longest open reading frame of the CD 38 splice variant LJ-2.

FIG. 7 shows the predicted longest open reading frame of the cDNA clone LJ-2 (starting from MET)

FIG. 8 shows the alignment of the longest open reading frame of the CD 38 splice variant LJ-2.

DETAILED DESCRIPTION OF THE INVENTION

Figure 1:
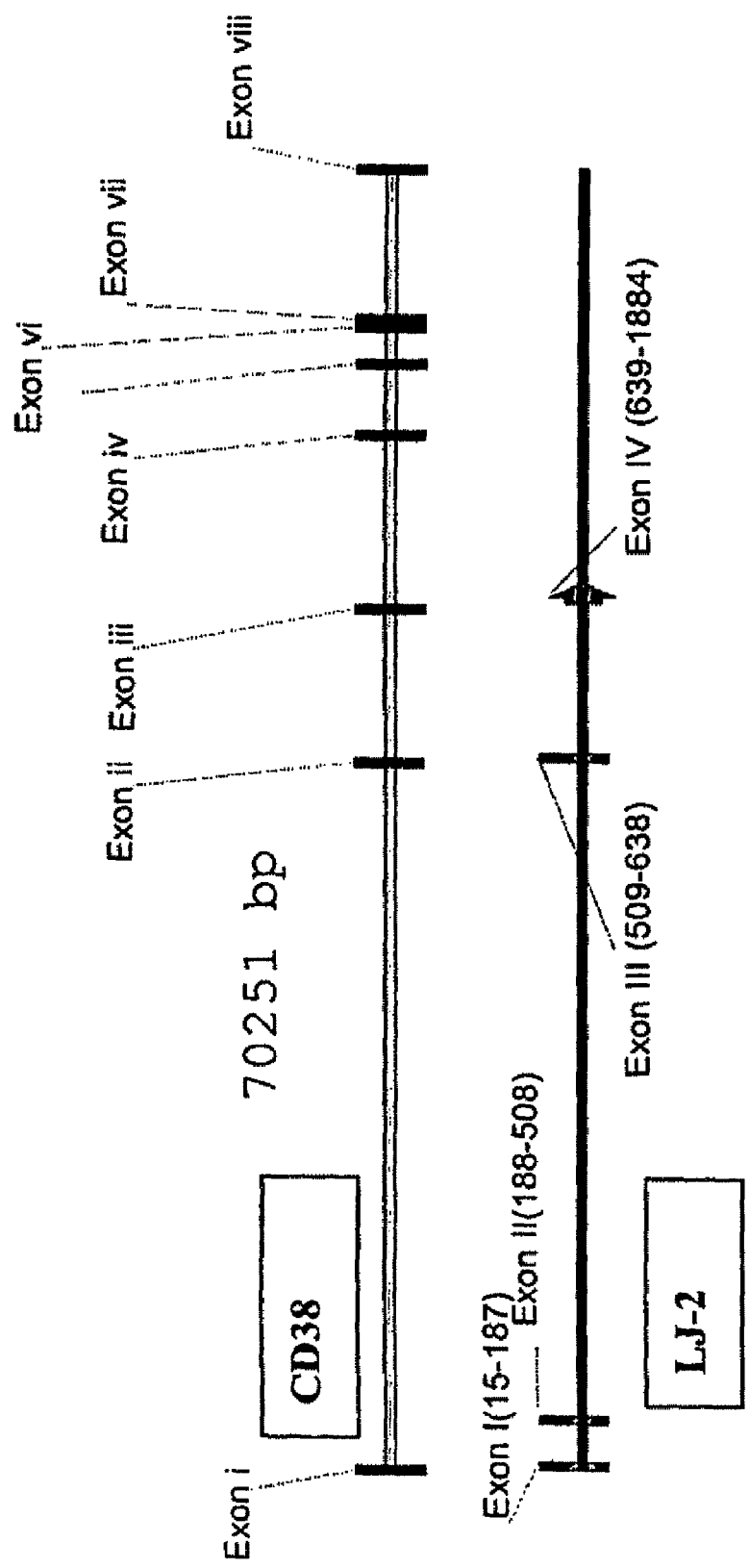
FIG. 1 shows the chromosomal mapping of the cDNA clone LJ-2.

It is understood that this invention is not limited to any particular, protocol, tools, and reagents as described, and that these may vary. It is also understood that the terminology used herein is for the purpose of describing particular embodiments only, and is not intended to limit the scope of the present invention.

Unless defined otherwise, all technical and scientific terms used herein are intended to have the same meanings as commonly understood by one of ordinary skill in the art in the field of the invention.

The use of the singular forms of the terms "a", "an," and "the" include plural reference unless the context clearly indicates otherwise.

In accordance with the present invention there may be employed conventional molecular biology, microbiology, and recombinant DNA techniques well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987). "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (Biochemistry, 1972, 11:1726-1732).

As used herein the term "CD38JL" refers to the amino acid sequences of substantially purified of the CD38 variant identified herein of any species and preferably mammalian species including man, from any source and either natural or synthetic.

As used herein the term "polypeptide" is used interchangeably with amino acid residue sequences or protein and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties.

As used herein, the term "cDNA" in the context of this invention refers to deoxyribonucleic acids produced by reverse transcription and typically second-strand synthesis of mRNA or other RNA produced by a gene. If double-stranded, a cDNA molecule has both a coding or sense and a non-coding or antisense strand.

The terms "fragment" of the present invention refer herein to proteins or nucleic acid molecules which can be isolated/purified, synthesized chemically or produced through recombinant DNA technology. All these methods are well known in the art. As exemplified herein below, the nucleotide sequences and polypeptides used in the present invention can be modified, for example by in vitro mutagenesis.

As used herein the term "agonist" means a molecule which when bound to CD38JL increases or prolongs the duration of the effect of CD38JL. An agonist may include proteins, nucleic acids, carbohydrates and any other molecule that may bind to and regulate the effect of CD38JL.

As used herein the term "antagonist," refers to a molecule which, when bound to CD38JL, decreases the amount or the duration of the effect of the biological or immunological activity of CD38JL. Antagonists may include proteins, nucleic acids, carbohydrates, antibodies, or any other molecules which decrease the effect of CD38JL.

As used herein the term "encoding" refers to the inherent property of specific sequences of nucleotides in a nucleic acid, to serve as templates for synthesis of other molecules having a defined sequence of nucleotides (i.e. rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for the transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns.

The terms "vectors" or "DNA construct" are commonly known in the art and refer to any genetic element, including, but not limited to, plasmid DNA, phage DNA, viral DNA and the like which can incorporate the oligonucleotide sequences, or sequences of the present invention and serve as a DNA vehicle into which DNA of the present invention can be cloned. Numerous types of vectors exist and are well known in the art.

The terminology "expression vector" defines a vector or vehicle as described above but designed to enable the expression of an inserted sequence following transformation into a host. The cloned gene (inserted sequence) is usually placed under the operation of control element sequences such as promoter sequences. Such expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

The term "oligonucleotide", as used herein refers to two or more molecules of deoxyribonucleotides adenine (A), guanine (G), thymine (T) and/or cytosine (C). The term "oligonucleotide" can be found in linear DNA molecules or fragments, viruses, plasmids, vectors, chromosomes or synthetically derived DNA. As used herein, DNA sequences are described according to the normal convention of giving only the sequence in the 5' to 3' direction.

As used herein the term "polynucleotide" of the present invention also includes those polynucleotides capable of hybridizing, under stringent hybridization conditions, to sequences contained in SEQ ID NO: 2 or the complement thereof. The term "stringent hybridization conditions" is used as generally understood in the art. For example the term can mean an overnight incubation at 42° C. in a solution comprising 50% formamide, 5×. SSC (750 mM NaCl, 75 mM trisodium citrate), 50 mM sodium phosphate (pH 7.6), 5×. Denhardt's solution, 10% dextran sulfate, and 20 mg/ml denatured, sheared salmon sperm DNA, followed by washing the filters in 0.1×SSC at about 60° C. The exact conditions required for "high stringency" may vary depending on the nature of the nucleic acid samples (i.e. DNA:DNA or DNA:RNA).

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH2PO4; 0.02M EDTA, pH 7.4), 0.5% SDS, 30% formamide, 100 mu·g/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

The conditions may be varied by adding or removing various blocking reagents. Blocking reagents can include Denhardt's reagent, heparin, BLOTTO, denatured salmon sperm DNA, and commercially available product. The inclusion of specific blocking reagents may require modification of the hybridization conditions described above, due to problems with compatibility.

The polynucleotide of the present invention can be composed of any polyribonucleotide or polydeoxribonucleotide, which may be unmodified RNA or DNA or modified RNA or DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

Two DNA sequences are "substantially complimentary" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

As used herein, the term "host" is meant to include not only prokaryotes but also eukaryotes such as yeast, plant and animal cells. A recombinant DNA molecule or gene which encodes a protein of the present invention can be used to transform a host using any of the techniques commonly known to those of ordinary skill in the art. Prokaryotic hosts may include *E. coli*, *S. tymphimurium*, *Serratia marcescens* and *Bacillus subtilis*. Eukaryotic hosts include yeasts such as *Pichia pastoris*, mammalian cells and insect cells.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to arrangements of CD38JL splice variant which are preferably about 5 to about 15 amino acids in length. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The terms "complementary" or "complementarity," as used herein, refer to the natural binding of polynucleotides under permissive salt and temperature conditions by base pairing.

The term "homology or identity," as used herein, refers to a degree of complementarity. There may be partial homology or complete homology. A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay under conditions of reduced stringency.

The phrases "percent identity" or "% identity" refer to the percentage of sequence similarity found in a comparison of two or more amino acid or nucleic acid sequences. Percent identity can be determined electronically, e.g., by using the MEGALIGN program (Lasergene software package, DNASTAR. Inc., Madison Wis.). The MEGALIGN program can create alignments between two or more sequences according to different methods, e.g., the clustal method. (Higgins, D. G. and P. M. Sharp (1988) Gene 73:237-244). Percent identity between nucleic acid sequences can also be calculated by the clustal method, or by other methods known in the art, such as the Jotun Hein method. (See, e.g., Hein, J. (1990) Methods in Enzymology 183:626-645.) Identity between sequences can also be determined by other methods known in the art, e.g., by varying hybridization conditions.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0$ t or $R_0$ t analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The term "microarray," as used herein, refers to an array of distinct polynucleotides or oligonucleotides arrayed on a substrate, such as paper, nylon or any other type of membrane, filter, chip, glass slide, or any other suitable solid support.

The term "substantially purified," as used herein, refers to nucleic acid or amino acid sequences that are removed from their natural environment and are isolated or separated, and are at least about 60% free, preferably about 75% free, and most preferably about 90% separated from other cellular or viral components. Thus, for example, a "purified protein" has been purified to a level not found in nature.

A "variant" of CD38JL, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

Using techniques including expression profile analysis, an EST AI989354 (SEQ ID NO: 9) which is highly induced in activated CD4+ T cells was identified. This EST sequence is located between known exons III and IV of the human CD38 gene. Using the EST AI989354 (SEQ ID NO: 9) as bait, a 1.9 kb cDNA clone (LJ-2) was isolated from a human peripheral lymphocyte cDNA library. The polynucleotide sequence for clone LJ-2 is shown in SEQ ID NO: 2. The cDNA sequence for LJ-2 was mapped on the CD38 gene locus on human chromosome 4 and found to share Exons I and II with CD38 (as shown in FIG. 1) and thus encodes a novel CD38 splice variant. FIG. 2 shows the alignment of polypeptides of CD38 and the CD38JL splice variant. The first 57 amino acids of CD38JL correspond to that of a portion of the CD38 sequence and the remaining amino acid residues (58-81) of CD38JL do not directly correspond to the CD38 sequence.

Figure 3:
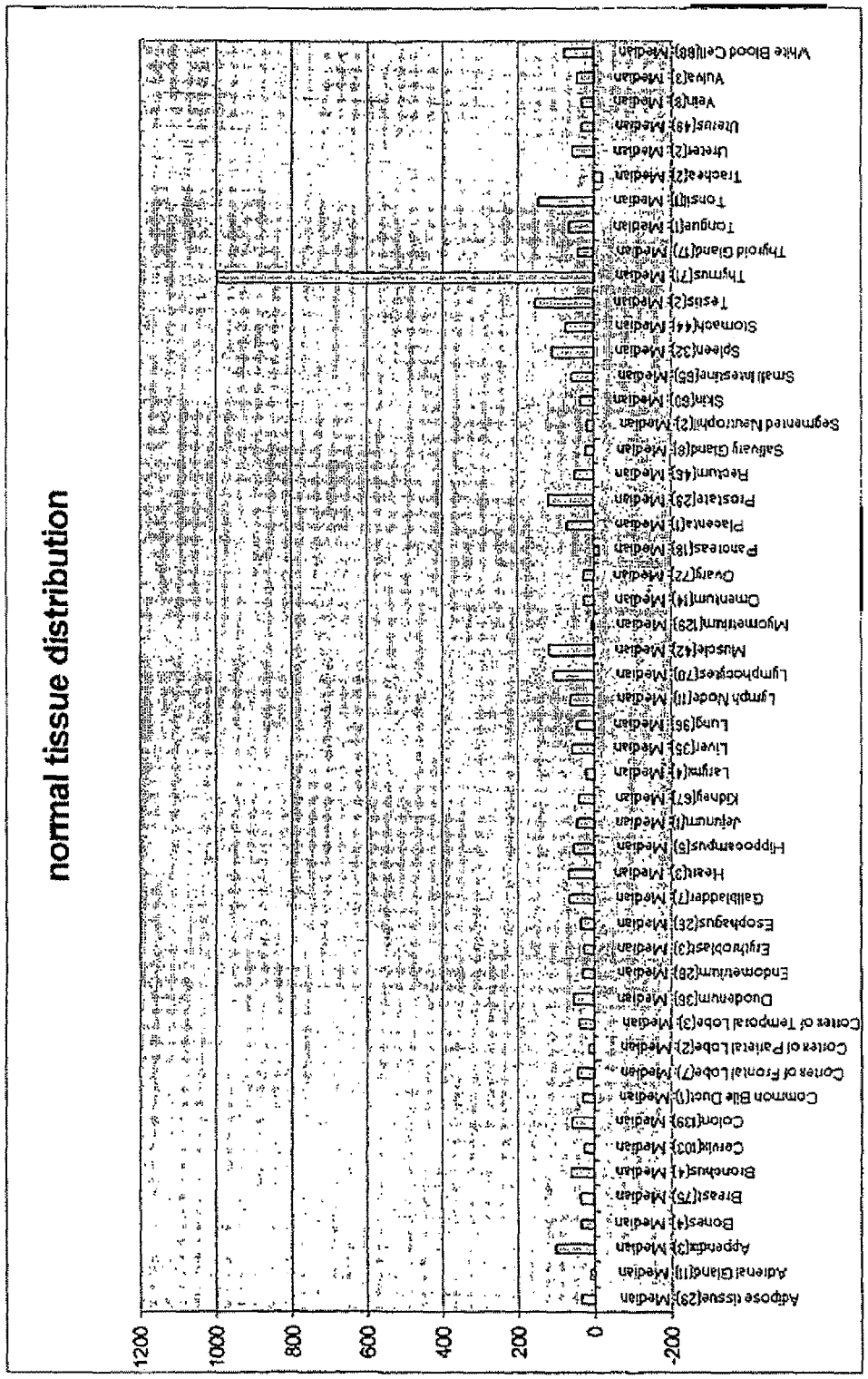
FIG. 3 shows the mRNA expression profile of A1989354 (SEQ ID NO: 9) in normal human tissues.

FIG. 3 shows the distribution of AI989354 expression in normal tissues. Data were obtained from affymetrix U95 genechip experiments according to the method as described in the Affymetrix Gene Chip® Expression Analysis Technical Manual. There is elevated expression of A1989354 in various tissues including the thymus.

Figure 4:
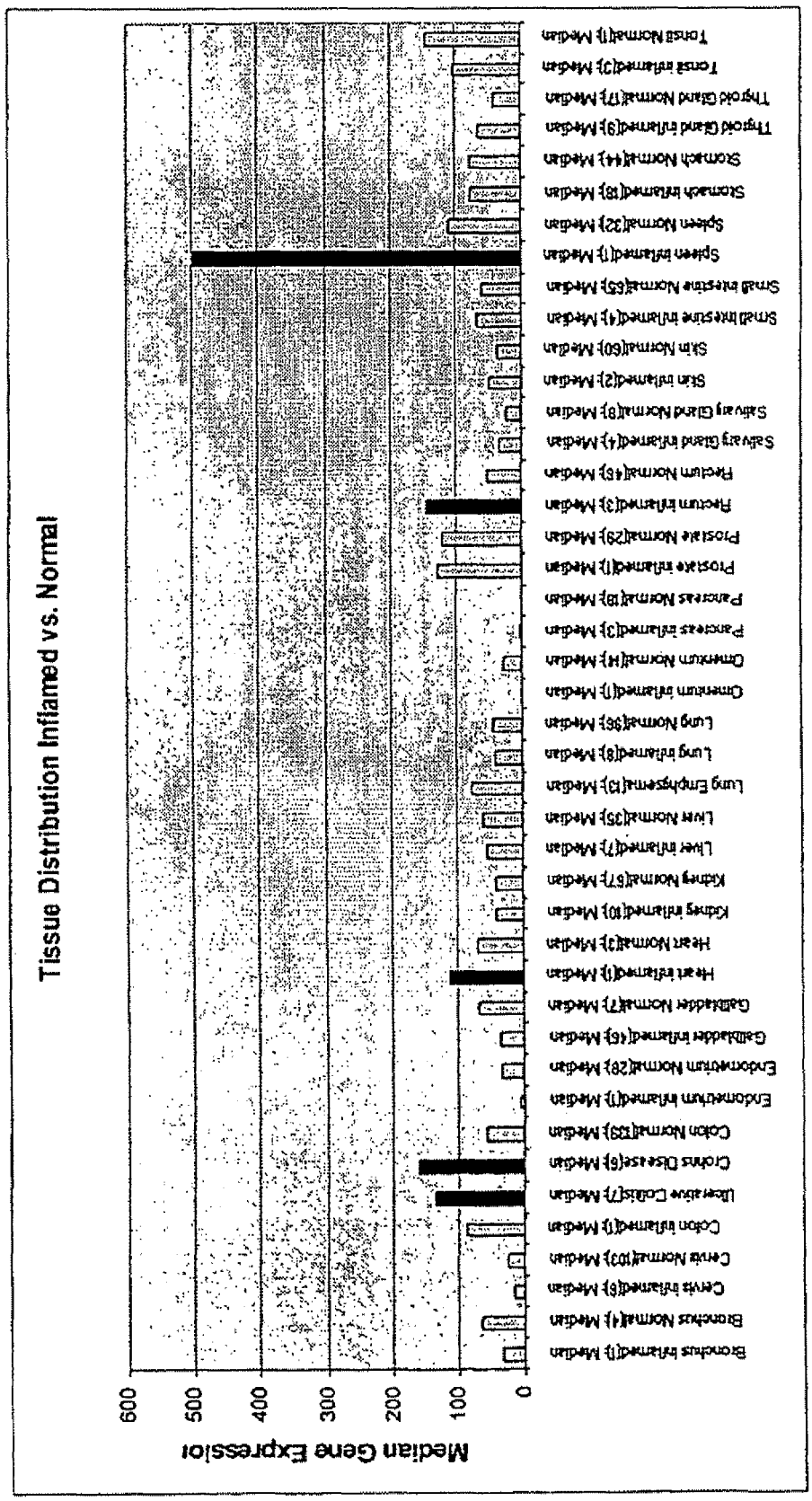
FIG. 4 shows mRNA expression of AI989354 (SEQ ID NO: 9) in various inflamed tissues vs. normal tissues.
Figure 5:
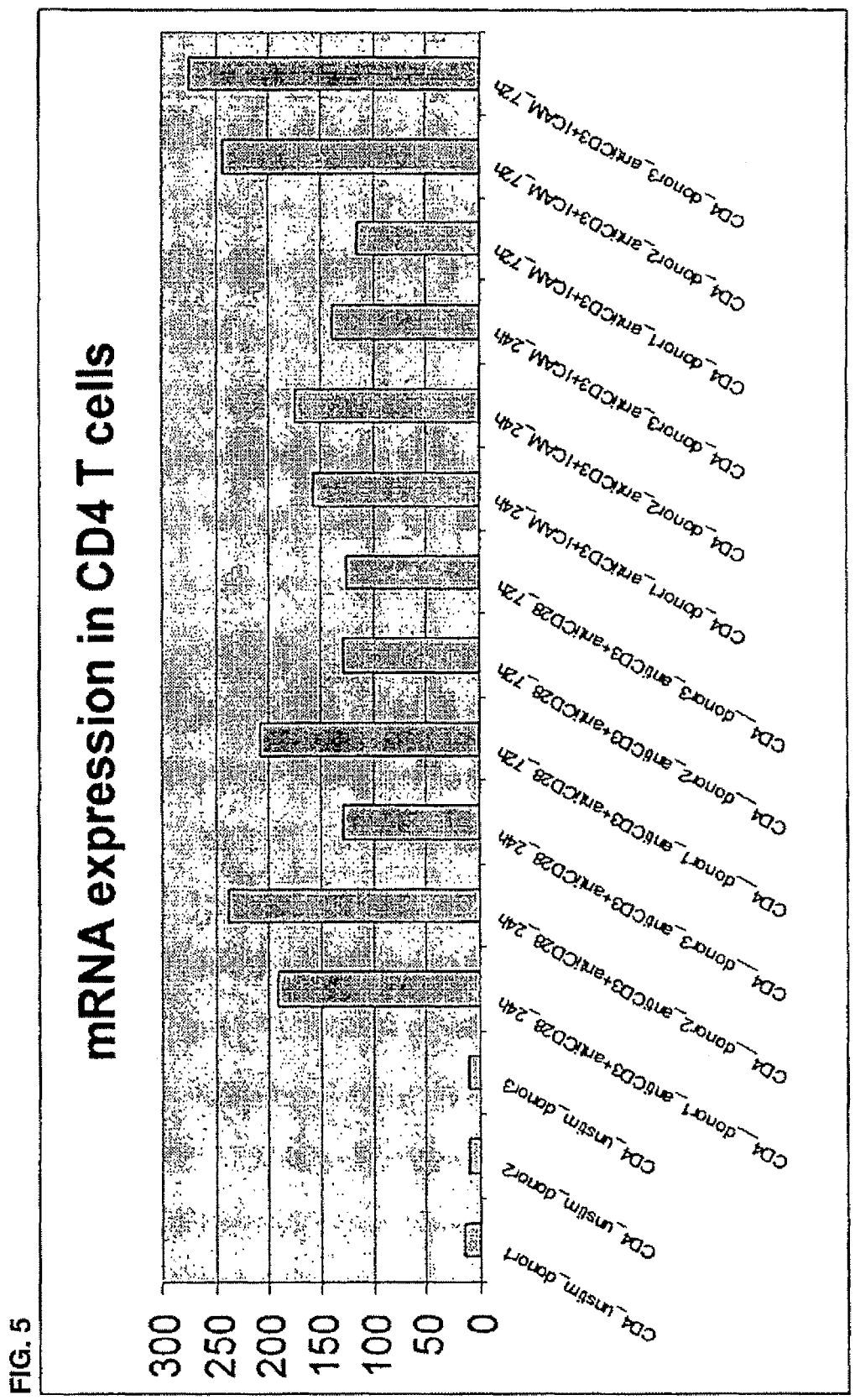
FIG. 5 shows mRNA expression profile of AI989354 (SEQ ID NO: 9) in stimulated and non-stimulated CD4+ T cells as measured by Affymatrix U95 genechip arrays.

FIG. 4 shows the distribution of A1989354 (SEQ ID NO: 9) expression in various inflamed tissues vs. normal tissues also obtained with Affymatrix analysis. CD38JL is also induced in tissues derived from patients with IBD and both Ulcerative Colitis and Chron's disease D. Enhanced expression in tissues of this origin suggests that the splice variant may play a role in T cell activation and may therefore provide a novel drug target for autoimmune and inflammatory disease. FIG. 5 shows the expression of AI989354 (SEQ ID NO: 9) in CD4 T cells as measured by Affymatrix U95 genechip arrays.

SEQ ID NO: 1 shows the 81 amino acid polypeptide predicted translate of the CD38 JL-2 cDNA. FIG. 6 shows the sequences of the CD38 translate starting with the first MET alongside the cDNA sequence of CD38JL cDNA. The exon positions including boundary are labeled, sequences different from CD38 are underlined.

One embodiment of the invention comprises an isolated polypeptide of amino acid sequence of SEQ ID NO: 1. CD38JL is 81 Amino acids long. As shown in FIG. 2 and FIG. 6, CD38JL bears homology to CD38 and has a potential ADP-ribosyl cyclase domain. The invention also encompasses derivatives of the CD38JL splice variant. A preferred derivative will have at least 90% polynucleotide identity to the polynucleotide encoding the polypeptide consisting of amino acid sequence of SEQ ID NO: 1. Any one of the polynucleotide variants described above can encode an amino acid sequence which contains at least one functional or structural characteristic of CD38JL.

The alignment of the longest open reading frame of the CD 38 splice variant LJ-2 (SEQ ID NOS 2 & 1 disclosed respectively in order of appearance) is shown below.

```
    <------------------------------------------------------------
  1 GAATTCGCAC CAGAAGAGCC CAACTCTGTC TTGGCGTCAG TATCCTGGTC CTGATCCTCG
    CTTAAGCGTG GTCTTCTCGG GTTGAGACAG AACCGCAGTC ATAGGACCAG GACTAGGAGC

----------------------exonI----------------------------------
 61 TCGTGGTGCT CGCGGTGGTC GTCCCGAGGT GGCGCCAGCA GTGGAGCGGT CCGGGCACCA
    AGCACCACGA GCGCCACCAG CAGGGCTCCA CCGCGGTCGT CACCTCGCCA GGCCCGTGGT
```

```
121 CCAAGCGCTT TCCCGAGACC GTCCTGGCGC GATGCGTCAA GTACACTGAA ATTCATCCTG
    GGTTCGCGAA AGGGCTCTGG CAGGACCGCG CTACGCAGTT CATGTGACTT TAAGTAGGAC

------><======================================================
181 AGATGAGAAA CAGCTAAAAG AAGTGAGTTG GGCCAGGCAC TGTGGCTCAC ACCTGTAATC
    TCTACTCTTT GTCGATTTTC TTCACTCAAC CCGGTCCGTG ACACCGAGTG TGGACATTAG

==============================================================
241 CCAGCACTTT GGGAGGCCCA GGCAGGTGGA TCACTTAAGG TCAGGAGTAC AAGACCTGCC
    GGTCGTGAAA CCCTCCGGGT CCGTCCACCT AGTGAATTCC AGTCCTCATG TTCTGGACGG

==============================================================
301 TGGCCAACAT GCTGAAACTC CGTCTCTACT AAAAATACAA AATTAGCCGG GTGTTGTGGC
    ACCGGTTGTA CGACTTTGAG GCAGAGATGA TTTTTATGTT TTAATCGGCC CACAACACCG

==============================================================
361 GCGTGCCTGT AATCCCAGCT ACTCTGGAGA CTGAGGTGGG AGAATCGCTT GAACCCAGGA
    CGCACGGACA TTAGGGTCGA TGAGACCTCT GACTCCACCC TCTTAGCGAA CTTGGGTCCT

==============================================================
421 GGAGGAGGTA GCACTGAACC AAGATCCAGC CTGGCCAAGA GAGTAAGACT CCGTCTCAAA
    CCTCCTCCAT CGTGACTTGG TTCTAGGTCG GACCGGTTCT CTCATTCTGA GGCAGAGTTT

=====exonII===================><------------------exonIII---------
481 ACCAAACCAA ACCAAACCAA AAAAAGAAAC ATGTAGACTG CCAAAGTGTA TGGGATGCTT
    TGGTTTGGTT TGGTTTGGTT TTTTTCTTTG TACATCTGAC GGTTTCACAT ACCCTACGAA -------------------------------------------------------------
541 TCAAGGGTGC ATTTATTTCA AAACATCCTT GCAACATTAC TGAAGAAGAC TATCAGCCAC
    AGTTCCCACG TAAATAAAGT TTTGTAGGAA CGTTGTAATG ACTTCTTCTG ATAGTCGGTG ----------------------------------------><<----------------------
        M  K  L  G  T  Q  T  V  P  C  N  K  I  L  L  W  S  R  I  K
601 TAATGAAGTT GGGAACTCAG ACCGTACCTT GCAACAAGAT TCTTCTTTGG AGCAGAATAA
    ATTACTTCAA CCCTTGAGTC TGGCATGGAA CGTTGTTCTA AGAAGAAACC TCGTCTTATT -----------------exonIV---------------------------------------
        D  L  A  H  Q  F  T  Q  V  Q  R  D  M  F  T  L  E  D  T  L
661 AAGATCTGGC CCATCAGTTC ACACAGGTCC AGCGGGACAT GTTCACCCTG GAGGACACGC
    TTCTAGACCG GGTAGTCAAG TGTGTCCAGG TCGCCCTGTA CAAGTGGGAC CTCCTGTGCG ---------------------------------------------------------<=====
        L  G  Y  L  A  D  D  L  T  W  C  G  E  F  N  T  S  S  E  A
721 TGCTAGGCTA CCTTGCTGAT GACCTCACAT GGTGTGGTGA ATTCAACACT TCCAGTGAGG
    ACGATCCGAT GGAACGACTA CTGGAGTGTA CCACACCACT TAAGTTGTGA AGGTCACTCC ===============================================================
        L  G  P  V  G  L  P  R  D  V  E  G  E  Q  S  D  F  C  W  R
781 CTCTGGGCCC TGTGGGATTG CCCAGGGATG TGGAGGGTGA ACAGAGTGAC TTCTGCTGGA
    GAGACCCGGG ACACCCTAAC GGGTCCCTAC ACCTCCCACT TGTCTCACTG AAGACGACCT ===============================================================
        P
841 GGCCCTGAAT GATTAGTGTG GAGGACAGAG CCACAGGCAC CCATCCTGAT GCCATCTATA
    CCGGGACTTA CTAATCACAC CTCCTGTCTC GGTGTCCGTG GGTAGGACTA CGGTAGATAT ===============================================================
901 CTTATATTAG TCCATTTGTG TTGCTATTAA GGAATACCTG AGGCTGCGTA ATTTATAAAG
    GAATATAATC AGGTAAACAC AACGATAATT CCTTATGGAC TCCGACGCAT TAAATATTTC ===============================================================
961 AAAAGAGGTT TATTTGACTC ACAGTTACGC AGGCTGTACA AGAAGTAGGG TACCAGCATC
    TTTTCTCCAA ATAAACTGAG TGTCAATGCG TCCGACATGT TCTTCATCCC ATGGTCGTAG ===============================================================
1021 CACTTCGGGT GAAGGCCTGA GGCTGTTTCC ACTCATGGAG AAGGGGAAGG GGAGCTGGCA
     GTGAAGCCCA CTTCCGGACT CCGACAAAGG TGAGTACCTC TTCCCCTTCC CCTCGACCGT ===============================================================
1081 TTTACAGAGA TCACATGGTG AGGGAGGAAA GCAAGGAGAG GTCAGGGGAG GTGCCAGGCT
     AAATGTCTCT AGTGTACCAC TCCCTCCTTT CGTTCCTCTC CAGTCCCCTC CACGGTCCGA ===============================================================
1141 GTTTGTAATG ACCAGCTGTC CTGGGAACTA GTAGAGTAAG AACTCATTAC TATAAGGACA
     CAAACATTAC TGGTCGACAG GACCCTTGAT CATCTCATTC TTGAGTAATG ATATTCCTGT ===============================================================
1201 GCACCATGCC ATTCGTGCAG GATCATCCCT ATGACCCAAA CACCTCCTAC TAGTCCCGAG
     CGTGGTACGG TAAGCACGTC CTAGTAGGGA TACTGGGTTT GTGGAGGATG ATCAGGGCTC
```

-continued

```
1261 CTCCAACACT GGGGGTCGAA TTTCAACATA AGGTTTGGAG AGTTAAATAT CCAAACTATA
     GAGGTTGTGA CCCCCAGCTT AAAGTTGTAT TCCAAACCTC TCAATTTATA GGTTTGATAT

1321 GCACTACCCT TAATGGCAAC TCAGGCTGAT ATAAAGTAGC ATTCCCTGTT TTCTTGAAAA
     CGTGATGGGA ATTACCGTTG AGTCCGACTA TATTTCATCG TAAGGGACAA AAGAACTTTT

1381 ATTGACTTCA GAGTTGGGGA TTGCCCATGC TCCCTAATTC CCTTCTTTTG AGTGCTCACA
     TAACTGAAGT CTCAACCCCT AACGGGTACG AGGGATTAAG GGAAGAAAAC TCACGAGTGT

1441 TAGCCTGCTT CCGAATTCTT GGTATTTTGC TCTCTGTAAG GTCATCATTC AGGTCCAAAG
     ATCGGACGAA GGCTTAAGAA CCATAAAACG AGAGACATTC CAGTAGTAAG TCCAGGTTTC

1501 AAGTCTAGAA CAGGATGAGG TCTCAGTGGG ACCTAGACCA AGGTTCTTGC TCTTCAGAAT
     TTCAGATCTT GTCCTACTCC AGAGTCACCC TGGATCTGGT TCCAAGAACG AGAAGTCTTA

1561 CATCACAGTA GCCATGGACT GGACTCTTCC ATCTCAGGCA CTGGCTTTGC CATCATTTTT
     GTAGTGTCAT CGGTACCTGA CCTGAGAAGG TAGAGTCCGT GACCGAAACG GTAGTAAAAA

1621 CAGATGTAGC CTTACCCTGC CCAGAAAGAC TCAACACCTC ACCAGGGGAA GGGATTTCCT
     GTCTACATCG GAATGGGACG GGTCTTTCTG AGTTGTGGAG TGGTCCCCTT CCCTAAAGGA

1681 ACAACCAAAA CCCTACTGCA GTTTTCACTT CTTTTTTTTT TCTTTTTGTT TATATGGTGG
     TGTTGGTTTT GGGATGACGT CAAAAGTGAA GAAAAAAAA AGAAAAACAA ATATACCACC

1741 ATATTTTTAC TTTATATAGT TTTATTCTTA TTTTTACTGT TTTTCATTGT TTGTTTTTAA
     TATAAAAATG AAATATATCA AAATAAGAAT AAAAATGACA AAAAGTAACA AACAAAAATT

1801 AAGCTTATCT TATTATAGCT TCTTTGTCCC AGGTTTGCAT TACTTTCAAT TACAAAAATA
     TTCGAATAGA ATAATATCGA AGAAACAGGG TCCAAACGTA ATGAAAGTTA ATGTTTTAT

=====================>
1861 AAGCATGATT ATTTGAAAAA AAAAAAAAAA AAAACTCGAC
     TTCGTACTAA TAAACTTTTT TTTTTTTTTT TTTTGAGCTG
```

It will be appreciated by those skilled in the art that a multitude of polynucleotide sequences encoding CD38JL, some bearing minimal homology to the polynucleotide sequences of any known and naturally occurring gene may be produced due to the degeneracy of the genetic code. Thus, the present invention also contemplates variations of polynucleotide sequence that could be made by selecting combinations based on alternative codon choices. These combinations are made in accordance with the standard triplet genetic code as applied to the polynucleotide sequence of naturally occurring CD38JL.

Although nucleotide sequences which encode CD38JL and its variants are preferably capable of hybridizing to the nucleotide sequence of the naturally occurring CD38 under appropriately selected conditions of stringency, it may be advantageous to produce nucleotide sequences encoding CD38JL or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding CD38JL without altering the encoded amino acid sequences include the production of RNA transcripts having more desirable properties, such as a greater half-life, than transcripts produced from the naturally occurring sequence.

The invention also encompasses production of DNA sequences which encode CD38JL and CD38JL derivatives, or fragments thereof, entirely by chemical synthesis chemists. Synthetic sequences may be inserted into expression vectors and host cell systems using reagents that are well known in the art. Moreover synthetic chemistry may be used to introduce mutations into a sequence encoding CD38JL or any fragment thereof.

Also encompassed by the invention are polynucleotide sequences that are capable of hybridizing to the claimed polynucleotide sequences, and, in particular, to those shown in SEQ ID NO: 2, or a fragment of SEQ ID NO: 2, under various conditions of stringency. (See, e.g., Wahl, G. M. and S. L. Berger (1987) Methods Enzymol. 152:399407; and Kimmel, A. R. (1987) Methods Enzymol. 152:507-511.)

CD38JL-encoding nucleotide sequences possessing non-naturally occurring codons may be used. For example, codons preferred by a prokaryotic host can be used to increase protein expression or to produce an RNA transcript having desirable properties, such as a half-life which is longer than that of a transcript generated from the naturally occurring sequence.

The nucleotide sequences of the present invention can be altered using methods generally known in the art in order to alter CD38JL-encoding sequences such as by cloning, processing, and/or expression of the gene product. Recombinant DNA techniques and synthetic oligonucleotides may be used to alter the nucleotide sequences.

In another embodiment of the invention, the polynucleotides encoding CD38JL, or derivative thereof, may be used for therapeutic purposes. In one aspect, the complement of the polynucleotide encoding CD38JL may be used in situations in which it would be desirable to block the transcription of the mRNA. In particular, cells may be transformed with sequences complementary to polynucleotides encoding CD38JL. Thus, complementary molecules or fragments may be used to modulate CD38JL activity. Such technology is now well known in the art, and sense or antisense, or siRNA, RNA interference oligonucleotides or larger fragments can be designed from various locations along the coding or control regions of sequences encoding CD38JL. RNA interference oligos and anti-sense oligos could be designed using the sequence of CD38 splice variant to specifically inhibit the function of the CD38 isoform. RNA interference is a process employing sequence-specific post-transcriptional gene silencing or gene knockdown by providing a double-stranded RNA (dsRNA) that is homologous in sequence to the targeted gene. Small interfering RNAs (siRNAs) can be synthesized in vitro or generated by ribonuclease III cleavage from longer dsRNA and are the mediators of sequence-specific mRNA degradation. SiRNA can be designed according to the technique described by Tuschl, described as follows. Elbashir, S M et al, Nature, 2001, 411, 494-498. Suitable siRNA for the instant invention can be double stranded ribonucleic acid comprising a first strand of nucleotides that is substantially identical to 19 to 25 consecutive nucleotides of SEQ ID NO. 2, and a second strand that is substantially complementary to the first.

The protein encoded by this novel CD38 variant could be selected for use in protein therapeutics. For example, monoclonal antibodies against CD38 splice variant polypeptides can be produced. Methods for producing monoclonal antibodies against isolated proteins and their administration to cells are known in the art. *Am J Gastroenterol.* 2002, 97:2962-72. Monoclonal antibodies directed against the CD38 splice variant polypeptides of the invention can be administered to cells to inhibit the function of the protein, and therefore to treat autoimmune or inflammatory diseases.

It is also contemplated that the CD38 splice variant of the present invention can be used in screening assays and ultra high throughput assays to identify small molecule inhibitors of the CD38 splice variant polypeptides. Small molecule inhibitors could block the binding of this CD38 variant to its cell surface receptor. It is known that CD38 is involved in adhesion and rolling of lymphocytes on endothelia cells through the interaction with CD31. [Dianzani, U., Stockinger, H., and Malavasi, F. (1998) *J Immunol* 160, 395402]. Therefore, blocking by small inhibitors in vivo could affect lymphocyte adhesion.

In another embodiment of the invention, natural, modified, or recombinant nucleic acid sequences encoding CD38JL may be ligated to a heterologous sequence to encode a fusion protein. For example, peptide libraries can be screened for inhibitors of CD38JL activity. It may also be useful to encode a chimeric CD38JL protein that can be recognized by antibodies that are commercially available. Fusion proteins may also be made to contain cleavage sites between the CD38JL encoding sequence and other heterologous protein sequence, so that CD38JL may be cleaved and purified away from the heterologous moiety.

Polypeptides

Polypeptide sequences encoding CD38JL or a fragment thereof may be synthesized, by employing chemical methods well known in the art. (See, e.g., Caruthers. M. H. et al. (1980) Nucl. Acids Res. Symp. Ser. 215-223, and Horn, T. et al. (1980) Nucl. Acids Res. Symp. Ser. 225-232.) Synthesized peptide may be substantially purified by preparative high performance liquid chromatography. (See, e.g, Chiez. R. M, and F. Z. Regnier (1990) Methods Enzymol. 182:392-421.)

The composition of the synthetic formed peptides may be confirmed by amino acid analysis or by sequencing. (See, e.g., Creighton, T. (1983) Proteins, Structures and Molecular Properties, W H Freeman and Co., New York, N.Y.)

Additionally, the amino acid sequence of CD38JL, or any part thereof, may be altered during direct synthesis and/or combined with sequences from other proteins, or any part thereof, to produce a variant polypeptide. It is also contemplated that CD38JL may be produced not only by direct peptide synthesis using solid-phase techniques. (See, e.g., Creighton, T. E. (1984) Protein: Structures and Molecular Properties, pp. 55-60, W. H. Freeman and Co., New York, N.Y.). Protein synthesis may be performed by manual techniques or by automation. Automated synthesis may be achieved, for example, using the Applied Biosystems 431A peptide synthesizer (Perkin Elmer). Fragments of CD38JL may be synthesized separately and then combined to produce the full length molecule.

CD38JL or its derivatives may be made by inserting cDNA sequences encoding into an expression vector with appropriate regulatory elements necessary for the transcription and translation of the inserted coding sequence according to methods known in the art. These methods include in vitro recombinant DNA techniques, synthetic techniques, and in vivo genetic recombination. (See, e.g., Sambrook, J. et al. (1989) Molecular Cloning, A Laboratory Manual, Cold Spring Harbor Press, Plainview, N.Y., ch. 4, 8, and 16-17; and Ausubel, F. M. et al. (1995, and periodic supplements) Current Protocols in Molecular Biology, John Wiley & Sons, New York, N.Y., ch. 9, 13, and 16.)

Fragments of CD38JL may be produced by recombinant production using techniques well known in the art. Host cells transformed with nucleotide sequences encoding CD38JL will be cultured under conditions suitable for the expression an isolation of CD38JL protein from cell culture. It is also understood that expression vectors containing nucleic acid sequences encoding CD38JL may be engineered to contain signal sequences that direct secretion of CD38JL through a the cell membrane or otherwise facilitate purification of the protein. Such purification domains include metal chelating peptides that allow for purification on immobilized metal, protein A domains that allow purification on immobliated immunoglobulin.

It is contemplated that polynucleotide probes derived from CD38JL polynucleotide sequences may be useful as probes or diagnostics for autoimmune and inflammatory conditions. Accordingly, the invention provides isolated and purified polynucleotides comprised of 10 or more bases selected from SEQ ID No: 1 and from bases 188-508 and 775-1884 of SEQ ID NO. 1.

Polynucleotide sequences encoding CD38JL may be used for the diagnosis of a disorder associated with expression of CD38JL splice variant. Examples of such diseases include IBD, and other inflammatory diseases such as IBD, Psoriasis, rheumatoid arthritis, and autoimmune diseases.

In another embodiment of the invention a vector capable of expressing CD38JL or a derivative thereof may be administered to a subject to treat or prevent an immunological disease.

In another embodiment, an agonist which modulates the activity of CD38JL may be administered to a subject to treat or prevent an immunological disease.

In another embodiment of the invention an antagonist which modulates the activity of CD38JL may be administered to a subject to treat or prevent an immunological disease. CD38JL antagonists may be produced using methods known in the art. An antagonist is believed to be more effective for the advantageous modulation of the CD38JL associated enzyme function. Either the agonist or the antagonist could work based on its function.

Purified CD38JL may be used to produce antibodies or to screen libraries of pharmaceutical agents to identify those which specifically bind CD38JL. CD38JL antibodies may also be generated using methods understood in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

Various hosts including goats, rabbits, rats, mice, humans, and others may be immunized by injection with CD38JL or with any fragment or oligopeptide thereof which has immunogenic properties and or antigenic determinants. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol.

Preferably oligopeptides, peptides, or fragments used to induce antibodies to CD38JL should have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Chimeric molecules comprised of short stretches of CD38JL and other proteins are also contemplated.

CD38JL monoclonal antibodies may be prepared using known methods for producing of antibody molecules by continuous cell lines in culture. These include, but are not limited to, hybridoma techniques, the human B-cell hybridoma techniques, and the EBV-hybridoma techniques. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; and Cole, S. P. et al. (1984) Mol. Cell Biol. 62:109-120.)

CD38JL antibodies may also be produced by inducing in vivo production in the lymphocyte cells or by screening immunoglobulin libraries or of highly specific binding reagents as disclosed in the literature. (See, e.g., Orlandi, R. et al. (1989) Proc. Natl. Acad. Sci. 86: 3833-3837; and Winter. G. et al. (1991) Nature 349:293-299.)

CD38JL specific antibodies may be identified using various immunoassays known in the art. Such immunoassays typically involve the measurement of antigen-antibody complex formation. A two-site, monoclonal-based immunoassay utilizing monoclonal antibodies reactive to two non-interfering CD38JL epitopes is preferred, but a competitive binding assay may also be employed. Antibodies to CD38JL may be useful as therapeutics in the treatment of inflammatory conditions. Thus in one embodiment of the invention provides A purified antibody that binds specifically to a poly peptide of SEQ ID. No. 1.

Diagnostics

In another embodiment, antibodies which specifically bind CD38JL may be used for the diagnosis of disorders characterized by expression of CD38 or CD38JL, or in assays to monitor patients being treated with CD38JL polypeptides agonists, antagonists, or inhibitors of CD38JL. Antibodies useful for diagnostic purposes may be prepared using methods described herein. Diagnostic assays for CD38JL include methods which utilize the antibody and a label to detect CD38JL in samples (tissue, cell, fluids) from in human body. The antibodies are then optionally modified and or labeled by covalent or non-covalent attachment of a reporter molecule.

A variety of protocols for detecting the presence of proteins such as CD38JL are known in the art including ELISAs, RIAs, and FACS. These methods can be used diagnose abnormal levels of CD38JL expression. Normal or standard values for CD38JL expression are established by combining body fluids or cell extracts taken from normal mammalian subjects, preferably human, with antibody to CD38JL under conditions suitable for complex formation. The amount of standard complex formation may be measured by various methods, preferably by photometric means. The levels of CD38JL that are expressed in subject, tissue samples are then compared with the standard values. The deviation between standard and subject values are calculated and used to establish the parameters for diagnosing disease.

The polynucleotides encoding CD38JL may be used for diagnostic purposes. The types of polynucleotides which may be used include oligonucleotide sequences, RNA and DNA molecules, and PNAs. The polynucleotides may be used to detect and quantify gene expression in tissues samples in which expression of CD38JL may be correlated with disease. The diagnostic assay may be used to determine absence, presence, and excess expression of CD38JL, and to monitor regulation of CD38JL levels during therapeutic intervention.

In one embodiment of the invention PCR probes directed to CD38JL specific sequence may be used to identify nucleic acid sequences which encode CD38JL. The specificity of the probe, whether it is made from a highly specific region, e.g., and the stringency of the hybridization or amplification (maximal, high, intermediate, or low), will determine whether the probe identifies only naturally occurring sequences encoding CD38JL, alleles, or related sequences.

Nucleic acid probes may also be used for the detection of related sequences, and preferably contain at least about 60% of the nucleotides from any of the CD38JL encoding sequences. The hybridization probes of the subject invention may be DNA or RNA and may be derived from the sequence of SEQ ID NO: 2.

Polynucleotide sequences encoding CD38JL may be used for the diagnosis of a disorder associated with expression of CD38JL.

Methods for Detecting and Measuring Expression of CD38JL

Methods for detecting and measuring expression of proteins such as CD38JL with polyclonal or monoclonal antibodies specific for the protein, are understood in the art. (See, e.g., Hampton, R. et al. (1990) Serological Methods, a Laboratory Manual, APS Press, St Paul, Minn., Section IV; and Maddox, D. E. et al. (1983) J. Exp. Med. 158:1211-1216). Preferred techniques include used include enzyme-linked immunosorbent assays (ELISAs), fluorescence activated cell sorting (FACS) and radioimmunoassays (RIAs). A two-site, monoclonal-based immunoassay utilizing monoclonal antibodies reactive to two non-interfering epitopes on CD38JL can be used as well as a competitive binding assay.

There are a number of labels and conjugation techniques that can be used in various nucleic acid and amino acid assays and these are known in the art. Means for producing labeled hybridization or PCR probes for detecting sequences related to polynucleotides encoding CD38JL include but are not limited to end-labeling, and PCR amplification using a labeled nucleotide. Alternatively, mRNA probes containing the sequences encoding CD38JL and derivatives thereof can be engineered using techniques known in the art. Such vectors are known in the art, are commercially available, and may be used to synthesize RNA probes in vitro by addition of an appropriate RNA polymerase. Reporter molecules or labels which may be used to detect molecules of interest include but are not limited to radionuclides, chromogenic agents, fluorescent, chemiluminescents.

General Administration and Pharmaceutical Compositions

The invention also provides methods of modulating CD38JL function in a patient comprising administering to the patient a compound according to the invention. If the purpose of modulating the CD38JL function in a patient is to treat a disease-state or condition, the administration preferably comprises a therapeutically or pharmaceutically effective amount of a pharmaceutically acceptable compound according to the invention. If the purpose of modulating the CD38JL function in a patient is for a diagnostic or other purpose (e.g., to determine the patient's suitability for therapy or sensitivity to various sub-therapeutic doses of the compounds according to the invention), the administration preferably comprises an effective amount of a compound according to the invention, that is, the amount necessary to obtain the desired effect or degree of modulation.

The compounds of the invention can be typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration can comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds can include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds can include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention can be formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Generally, a therapeutically effective daily dose would be from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day, and most preferably from about 7.0 mg to about 105 mg per day. Some degree of routine dose optimization may be required to determine an optimal dosing level and pattern.

Pharmaceutically acceptable carriers and excipients encompass all the foregoing additives and the like.

EXAMPLES OF THE INVENTION

Example 1

Microarray Analysis of CD4+ Cells

Human CD4+ T cells were purified from peripheral blood obtained from donors and stimulated by anti-CD3 antibody+ anti-CD28 antibody, or anti-CD3 antibody+ ICAM for 24 hours or 72 hours. The unstimulated cells are used as controls. Total RNA from these cells were extracted and quantified by analysis using Affymetrix U95 gene chips. We performed expression profile analysis and identified that EST (AI989354) (SEQ ID NO: 9) is expressed highly induced during T cell activations (either by anti-CD3+ anti-CD28 or by anti-CD3+ ICAM) (FIG. 5). The data were confirmed by T cell samples from three different donors.

Example 2

Microarray Analysis of Normal Tissues

The expression profile of the gene AI989354 (SEQ ID NO: 9) in normal tissues were also obtained by Affymetrix U95 genechip experiments. RNA samples from multiple donors were used for each group of normal tissues. AI989354 (SEQ ID NO: 9) is highly expressed in normal thymocytes (FIG. 3), suggesting that it is important function in T cells and immune systems. The expression of A1989354 (SEQ ID NO: 9) in all other tested normal tissues was relatively low (FIG. 3). The selective expression in Thymus suggests that this gene has important immune functions and that this gene might make a good target because its modulation by inhibitors, antagonist or agonists would have less side effects due to its low expression in other tissues.

Example 3

Isolation and Sequencing of LJ-2

The plasmid clone LJ-2 was isolated from the human peripheral blood leukocyte (PBL) cDNA library array panels in the "Longest-Clone" cDNA library screening (Origene Technologies Inc, Rockville, Md.). The human cDNA fragments were inserted into a vector, pCMV6-XL4, which size is 4.7 kb to construct the cDNA library. Approximately 6 million size-selected clones, derived from twelve human tissue library panels consisting of fetal and adult brain, heart, kidney, liver, lung, muscle, peripheral blood leukocytes, placenta, small intestine, spleen, and testis, were arrayed into the 96-well "super plate". Each well of the super plate contains 40,000 clones. For the library screen, three PCR primers were designed from AI989354 (SEQ ID NO: 9) sequences

```
SEQ. ID. NO: 3:
P1R (reverse primer)         GAGGTGTTGAGTCTTTCTGGGCA

SEQ. ID. NO: 4:
P2F (forward primer),        ATAGCCTGCTTCCGAATTCTTGG

SEQ. ID. NO: 5:
P3F (forward primer),        CCCATGCTCCCTAATTCCCTTC

SEQ. ID. NO: 6:
VP3F (forward primer         GACAGAGCTCGTTTAGTGAACC
vector)

SEQ. ID. NO: 7:
VP6R (reverse primer         TAGAAGGACACCTAGTCAGAC
vector)
```

The super plate was screened by PCR using the pair of P3F/P1R primers. The positive wells were then rescreened using a pair of VP3F/P1R primers to identify the well with the longest clone.

This well corresponds to a "master plate", which contains 5,000 clones per well. The master plate was also screened using the VP3F/P1R primers to identify the well with the longest clone. The appropriate 96-well sub-plate, derived from the selected well of the master plate and containing 50 clones per well, was screened by PCR using the P3F/P1R primers. Cells from the positive sub-plate well were then plated out and 96 individual colonies were picked and screened by PCR to identify the final clone using primer pairs of P3F/P1R, VP3F/P1R, P2F/VP6R, and P3F/VP6R. PCR products were amplified from one clone, LJ-2, by P3F/P1R (~436 bp), VP3F/P1R (~1.7 kb), P2F/VP6R (~590 bp), and P3F/VP6R (~620 bp), respectively. The LJ-2 sequence which contains AI989354 (SEQ ID NO: 9) sequence was obtained by sequencing the insert of clone LJ-2.

Example 4

Microarray Analysis of AI989354 (SEQ ID NO: 9) Expression in Various Inflamed Tissues Vs. Normal Tissues The mRNA expression of the gene AI989354 (SEQ ID NO: 9) in a number of inflamed and normal control tissues were also obtained by Affymetrix U95 genechip experiments. AI989354 (SEQ ID NO: 9) expression is induced in inflamed colon tissues from inflamed bowel disease patients (comparing colon tissues from 6 Crohn's Disease patients and 7 Ulcerative Colitis patients versus 39 normal colons) (FIG. 4). The gene is also induced in inflamed rectum and inflamed spleen as compared to the normal controls (FIG. 4). The induced expression of AI989354 (SEQ ID NO: 9) in these inflamed tissues suggests that AI989354 (SEQ ID NO: 9) may mediate inflammatory responses in these tissues.

Example 5

Sequence Search Against Database

A search of the SEQ ID NO: 1 against the InterPro database using the INTERPRO program was performed in order to obtain protein families, domains or sites that have a high degree of similarity to SEQ. ID NO: 1 This search revealed two protein families the PFO2267 family and the SSF56629 family. The PF02267 family encodes a polypeptide having an ADP-ribosyl cyclase CD38/157. The e-value for PFO2667 5.9e-05. The SSF56629 family also has a ADP-ribosyl cyclase region. For SSF56629 the E-value was: 9e-23.

---

The invention claimed is:

1. A substantially purified polynucleotide which is
   (a) a polynucleotide which encodes a polypeptide comprising the amino acid sequence of SEQ ID NO: 1; or
   (b) a polynucleotide which encodes a polypeptide fragment comprising amino acids 58-81 of SEQ ID NO: 1.

2. An expression vector which comprises the polynucleotide of claim 1.

3. The expression vector of claim 2 which encodes the polypeptide of SEQ ID NO: 1 or said polypeptide fragment comprising amino acids 58-81 of SEQ ID NO: 1 when expressed in a host cell.

4. A substantially purified polynucleotide of claim 1, which encodes a polypeptide comprising the amino acid sequence of SEQ ID NO: 1.

5. A substantially purified polynucleotide of claim 1, having the sequence of SEQ ID NO:2.

* * * * *